(12) United States Patent
Skubitz et al.

(10) Patent No.: US 9,168,371 B2
(45) Date of Patent: Oct. 27, 2015

(54) FEATURES FOR ROUTING CONDUCTORS IN MEDICAL ELECTRICAL LEAD ELECTRODE ASSEMBLIES

(71) Applicant: Medtronic, Inc., Minneapolis, MN (US)

(72) Inventors: Sean P. Skubitz, Forest Lake, MN (US); Mary L. Boatwright, Andover, MN (US); Stephen L. Bolea, Watertown, MN (US); Jessica L. Tower, Minneapolis, MN (US); Michael E. Metzler, Eden Prairie, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 3 days.

(21) Appl. No.: 14/146,326

(22) Filed: Jan. 2, 2014

(65) Prior Publication Data
US 2014/0114386 A1 Apr. 24, 2014

Related U.S. Application Data

(60) Continuation of application No. 12/783,199, filed on May 19, 2010, now Pat. No. 8,634,893, which is a division of application No. 11/465,946, filed on Aug. 21, 2006, now Pat. No. 7,738,966.

(51) Int. Cl.
*A61N 1/05* (2006.01)

(52) U.S. Cl.
CPC ......... *A61N 1/0553* (2013.01); *Y10T 29/49117* (2015.01)

(58) Field of Classification Search
USPC ........... 607/1, 36–37, 115–116; 600/373–391
See application file for complete search history.

*Primary Examiner* — Deborah Malamud
(74) *Attorney, Agent, or Firm* — Withers & Keys, LLC

(57) ABSTRACT

An insulative body of a medical electrical lead electrode assembly includes a pre-formed channel having a section extending at an angle to a longitudinal axis of the body. An electrode portion of a conductive component has an electrode contact surface facing outward from a first side of the body and a coupling portion embedded in the body. A conductor, which is coupled to the coupling portion of the component, is disposed in the channel.

16 Claims, 11 Drawing Sheets

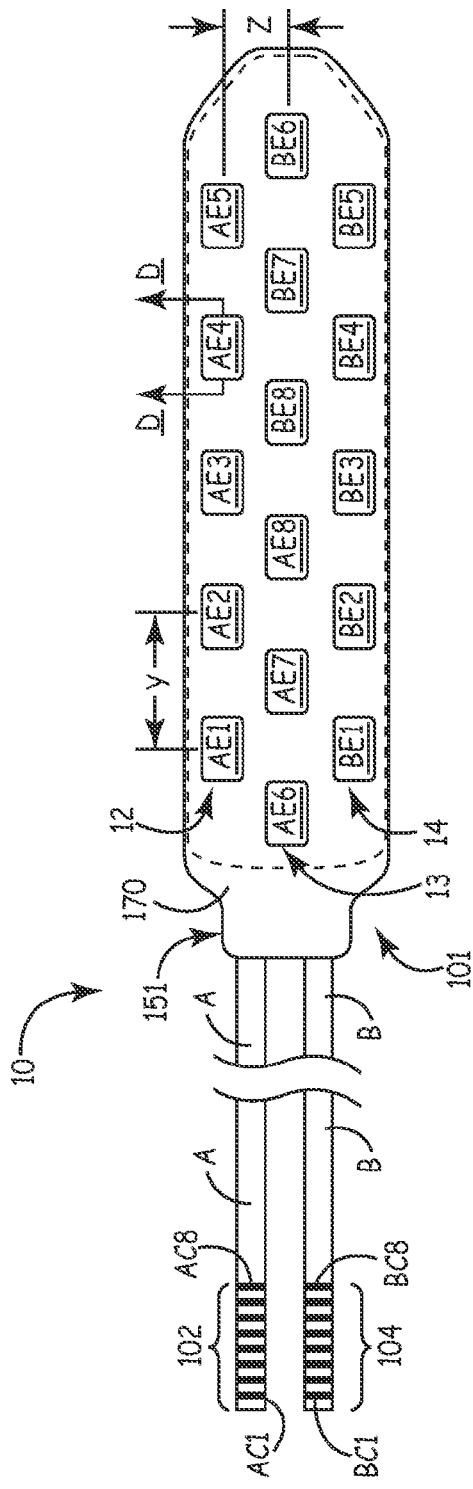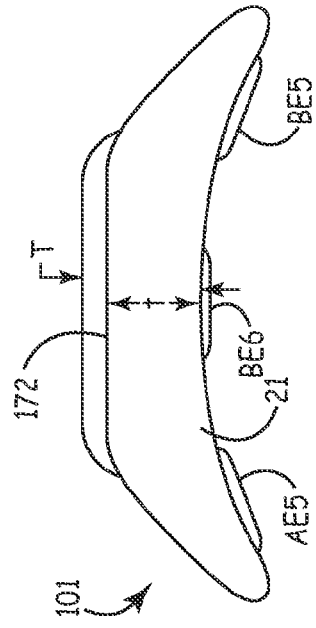
FIG. 1A
FIG. 1B

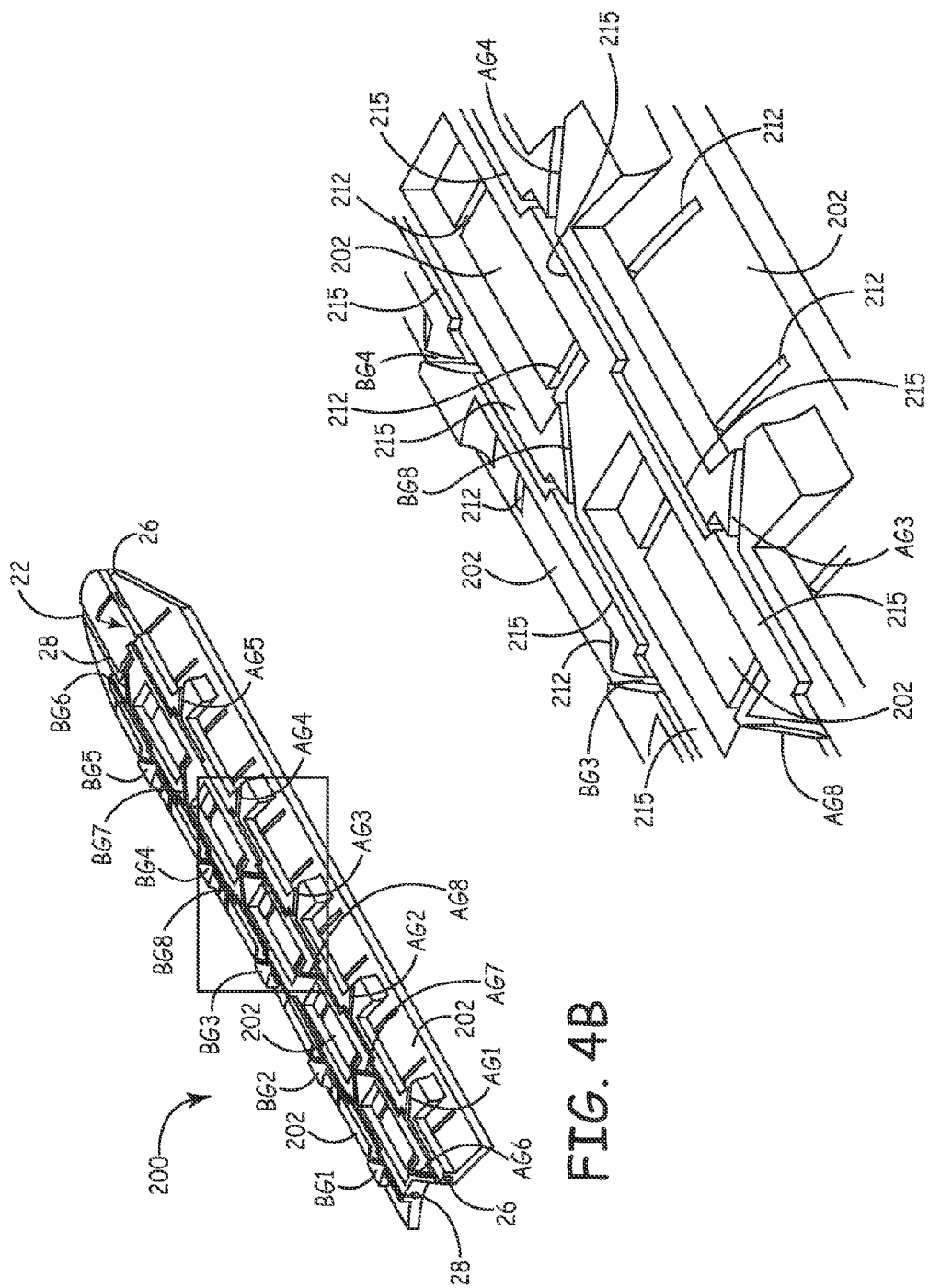

FEATURES FOR ROUTING CONDUCTORS IN MEDICAL ELECTRICAL LEAD ELECTRODE ASSEMBLIES

RELATED APPLICATIONS

The present application is a divisional of U.S. patent application Ser. No. 11/465,946, filed Aug. 21, 2006, now allowed. The present application is related to two commonly-assigned applications: U.S. patent application Ser. No. 11/465,941, filed Aug. 21, 2006 (U.S. Patent Publication No. 2008/0046050, published Feb. 21, 2008) entitled "NOVEL MEDICAL ELECTRODE MOUNTING"; and U.S. patent application Ser. No. 11/465, 879, filed Aug. 21, 2006 (U.S. Patent Publication No. 2008/0046049, published Feb. 21, 2008), entitled "NOVEL ASSEMBLY FOR MEDICAL ELECTRICAL LEADS", both of which are hereby incorporated by reference in their entireties.

TECHNICAL FIELD

The present disclosure is related to medical electrical leads and more particularly to electrode assemblies thereof.

BACKGROUND

Medical electrical leads include one or more conductors that extend within an elongate insulative body and are coupled to one or more electrodes supported by the body. The one or more electrodes are typically mounted to a distal portion of the lead body and the distal portion positioned, or implanted, in a patient's body to provide electrical stimulation, for example, within a pericardial space, to provide restorative cardiac stimulation, or, within an epidural space, to provide pain-relieving spinal stimulation.

The portion of the lead body that supports the one or more electrodes should be configured to, at minimum, allow each electrode surface to make contact with a target stimulation site, support each joint between the one or more electrodes and the corresponding conductor, and, in the case of more than one electrode, electrically isolate the electrodes and conductors from one another. Electrode assemblies have been developed, for example, within the context of the exemplary stimulation scenarios referenced above, wherein a 'flattened', or relatively thin, lead body portion, for example, having a patch or paddle configuration, supports one or more electrodes, preferably an array of electrodes, that are disposed along a major surface of the lead body portion. However there is still a need for electrode assembly features that improve the routing of conductors from the electrodes.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments of the present disclosure will hereinafter be described in conjunction with the appended drawings, wherein like numerals denote like elements.

FIG. 1A is a plan view of an exemplary medical electrical lead, according to some embodiments of the present disclosure.

FIG. 1B is an end view of the lead shown in FIG. 1A.

FIG. 4B is a perspective view of an insulative carrier showing a second side thereof, according to some embodiments of the present disclosure.

FIG. 4C is an enlarged view of a portion of the carrier shown in FIG. 4B.

DETAILED DESCRIPTION

Figure 2A:
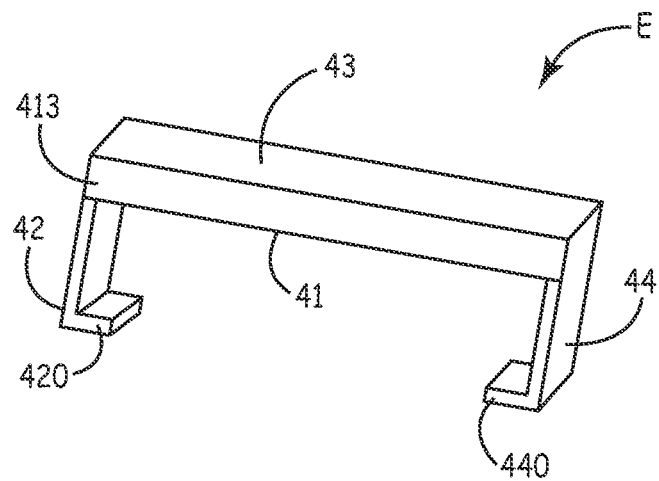
FIG. 2A is a perspective view of a conductive component, according to some embodiments of the present disclosure.

The following detailed description is exemplary in nature and is not intended to limit the scope, applicability, or configuration of the disclosure in any way. Rather, the following description provides practical illustrations for implementing exemplary embodiments of the present disclosure. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

FIG. 1A is a plan view of an exemplary medical electrical lead 10, according to some embodiments of the present disclosure; and FIG. 1B is an end view of lead 10. FIG. 1A illustrates lead 10 including a pair of elongate insulative tubular bodies A and B which are terminated at a proximal end by connectors 102 and 104, respectively, and which extend distally to terminate in an insulative paddle-shaped body 101 supporting an array of electrodes AE1-8 and BE1-8, which are arranged in three columns 12, 13, and 14. FIG. 1B illustrates a profile of body 101, which has a maximum thickness T of approximately 0.09 inch along a proximal portion 151 thereof, and a maximum thickness t of approximately 0.075 inch along a length thereof that extends distally from proximal portion and corresponds with an extent of columns 12, 13, 14. The shape and profile of body 101 makes lead 10 suitable for epidural implantation to provide spinal cord stimulation; and the arrangement of electrodes AE1-8 and BE1-8 can provide flexibility for selection of a stimulation pattern from a variety of stimulation patterns after lead 10 is implanted, without having to physically reposition lead 10.

According to an exemplary embodiment of the present disclosure, each electrode in columns 12, 13 and 14 are spaced apart from one another, along a length of each column, by a distance x, center-to-center, which is approximately 0.120 inch, and each column 12, 13, 14 is spaced apart from one another by a distance z, center-to-center, which is approximately 0.179 inch. Although the electrode array illustrated herein provides a suitable example for preferred embodiments of the present disclosure, it should be noted that various alternate embodiments of the present disclosure include any number of electrodes in any arrangement.

According to the illustrated embodiment, electrodes AE1-8 are coupled to corresponding contacts AC1-8 of connector 102 and electrodes BE1-8 are coupled to corresponding contacts BC1-8 of connector 104, such that each electrode may be independently powered when the connectors 102, 104 are plugged into a stimulation device. Although not shown, those skilled in the art will appreciate that conductors A1-8 (FIG. 5), which couple each of electrodes AE1-8 to a corresponding contact of connector 102, extend within one or more longitudinally extending pre-formed channels, or lumens, of tubular body A, and conductors B1-8 (FIG. 5), which couple each of electrodes BE1-8 to a corresponding contact of connector 104, extend within a similar one or more channels, or lumens, of tubular body B. Each of conductors A1-8 and B1-8 may be in the form of a coil or cable, being formed, for example from MP35N alloy, and each preferably includes an insulating jacket extending thereover, being formed, for example, from a fluoropolymer; such conductors are well known to those skilled in the art of medical electrical leads. A routing of the conductors within body 101, according to one embodiment of the present disclosure, will be described below, in conjunction with FIG. 5.

FIG. 1A further illustrates, with a dashed line, a border of an insulative carrier 200 (FIGS. 4A-D), preferably formed from a flexible polymer, for example, silicone rubber which may have a polyester mesh panel embedded therein. According to the illustrated embodiment, carrier 200 is coupled to an insulative layer 170 to form body 101, and layer 170 is preferably formed from a material similar to that which forms carrier 200. FIG. 1B further illustrates a first side 21 of carrier 200 corresponding to a side of body 101 from which electrodes AE1-8, BE1-8 may protrude, as illustrated; alternately, electrodes AE1-8, BE1-8 may be flush with first side 21 or recessed within first side 21. Insulative layer 170 is shown extending over a second side 22 (FIG. 4B) of carrier 200 to form an opposite side 172 of body 101, and further extends about distal portions of bodies A,B to form proximal portion 151, for example, as described below in conjunction with FIG. 5. According to embodiments of the present disclosure, each electrode AE1-8, BE1-8 is a portion 413 of a conductive component E, preferably formed from a 90/10 Platinum/iridium alloy, various embodiments of which are described in conjunction with FIGS. 2A-B, 3A-C, 6A-B and 7A-B.

Figure 2B:
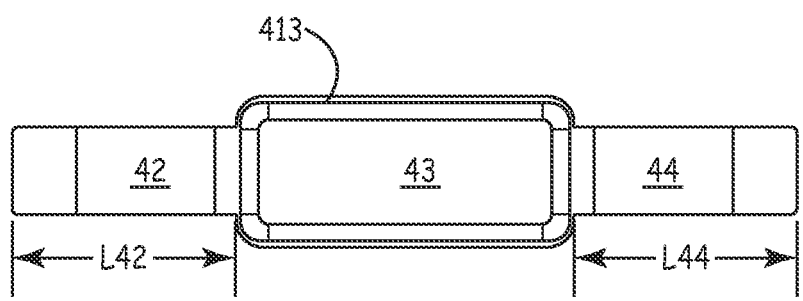
FIG. 2B is a plan view of a conductive component, according to some embodiments of the present disclosure.

FIGS. 2A-B illustrate electrode portion 413 of component E including an outward facing contact surface 43 and an inward facing surface 41; a pair of tabs 42, 44 extend from electrode portion 413 and are adapted to extend through carrier 200 in order to couple component E thereto. FIG. 2A further illustrates each tab 42, 44 including a projection 420, 440, respectively. According to some embodiments of the present disclosure, component E is formed, for example, by stamping, such that portion 413, tabs 42, 44 and projections 420, 440 are approximately co-planar with one another, for example as shown in FIG. 2B; then, tabs 42, 44 and projections 420, 440 are folded or bent away from portion 413 into the configuration illustrated in FIG. 2A. Creases or indentations, for example, as illustrated by dashed lines in FIG. 2B, may be formed in tabs 42, 44 in order to guide subsequent folding or bending. Alternately, component E may be provided as illustrated in FIG. 2A by a single forming step, for example, machining or any other suitable forming method known to those skilled in the art. According to exemplary embodiments of the present disclosure, electrode portion 413 has a length, from tab 42 to tab 44, of approximately 0.185 inch, and a width of approximately 0.086 inch; and tabs 42, 44 each have a thickness of approximately 0.005 inch, and a length, from electrode portion 413 to projections 420, 440, respectively, of approximately 0.094 inch; and projections each have a length of approximately 0.028.

Figure 3A:
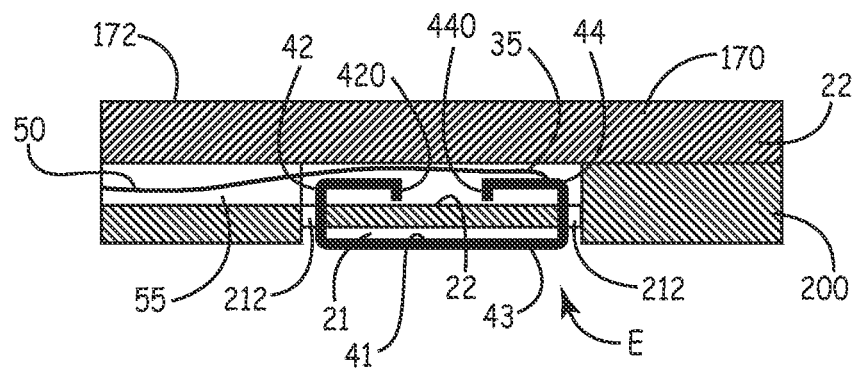
FIG. 3A-B are section views taken through section line D-D of FIG. 1A, according to some alternate embodiments of the present disclosure.

FIG. 3A is a section view, through section line D-D of FIG. 1A, wherein component E is coupled to carrier 200, according to some embodiments. FIG. 3A illustrates each of tabs 42, 44, having been inserted through openings 212 of carrier 200, extending to second side 22 of carrier 200 where tabs 42, 44 are bent toward a surface of second side 22, such that tabs 42, 44 extend along the surface of second side 22, opposite inward facing surface 41 of the electrode portion that is disposed against a surface of first side 21 of carrier 200, and projections 420, 440 extend toward the surface of side 22. Pre-formed openings, for example, openings 212, may be sized to accommodate tabs 42, 44 including projections 420, 440, or any other tab cross-section for that matter; or, carrier 200 may be stretched to widen the pre-formed openings for insertion of tabs 42, 44 including projections 420, 440, or tabs having larger cross-sections that the openings. According to alternate embodiments, tabs 42, 44 do not include projections 220, 240. Furthermore, it should be noted that embodiments of the present disclosure need not include pre-formed openings, for example, openings 212 in carrier 200 for tabs 42, 44 to pass through, since tabs 42, 44 may form the openings by piercing carrier 200 upon insertion therethrough.

Figure 3B:
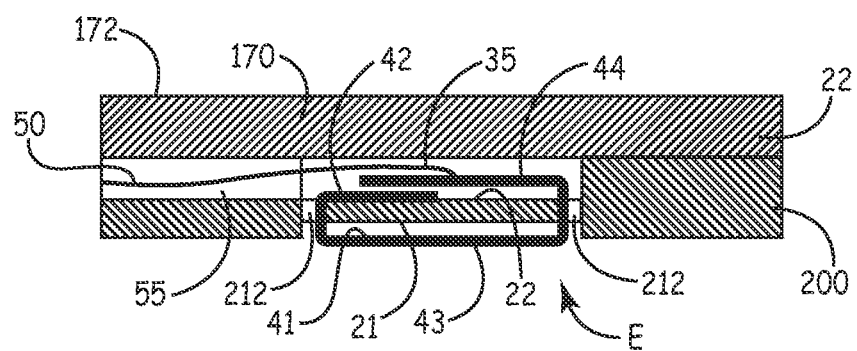
Figure 6A:
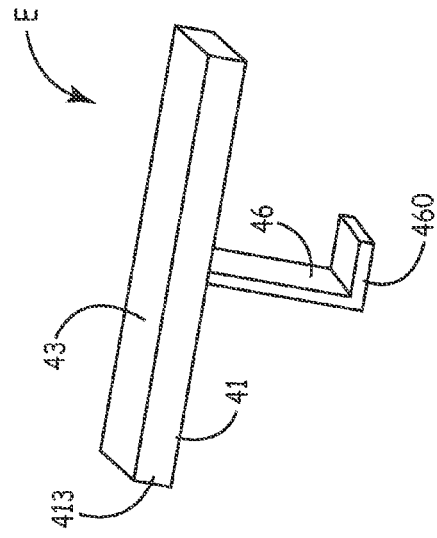
FIGS. 6A-B are perspective views of a conductive component, according to further alternate embodiments of the present disclosure.
Figure 6B:
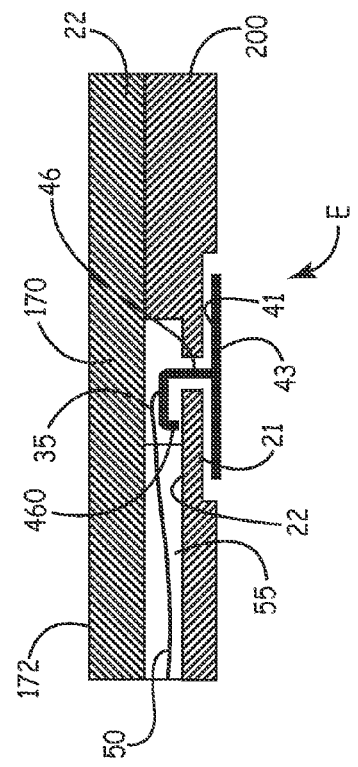
Figure 7A:
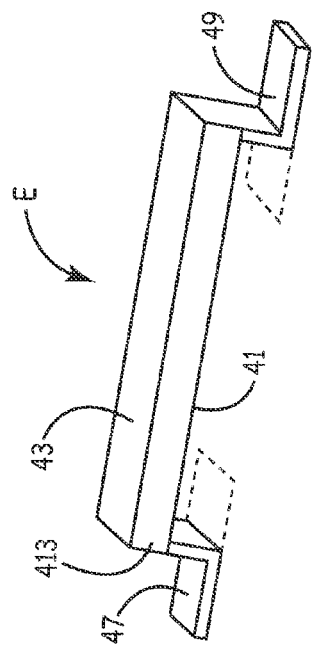
FIGS. 7A-B are section views taken through section line D-D of FIG. 1A, according to further alternate embodiments of the present disclosure.
Figure 7B:
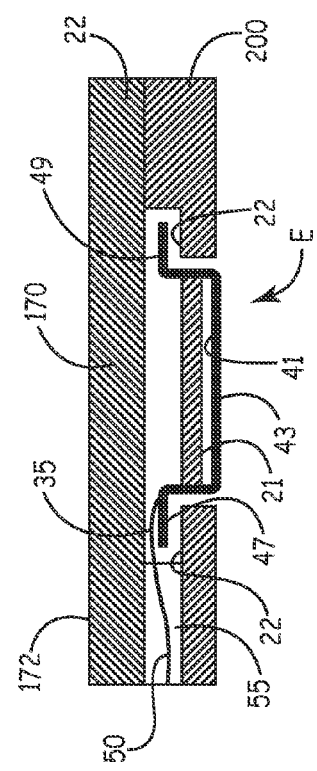

Referring back to FIG. 2B, a length L42, L44 of each tab 42, 44, respectively, is indicated. According to further alternate embodiments of the present disclosure, length L44 is greater than length L42 such that when tabs 42, 44 are bent toward the surface of second side 22, tab 44 overlaps tab 42, as illustrated in FIG. 3B. According to an exemplary embodiment wherein tabs overlap, a length of electrode portion 413, between tabs 42, 44 is approximately 0.185 inch, length L44 of tab 44 is approximately 0.195 inch, and length L42 of tab 42 is approximately 0.167 inch. (Another alternate embodiment of component E is described below, in conjunction with FIG. 3C. Further embodiments of component E coupled to carrier 200, which generally correspond to additional alternate embodiments of component E, shown in FIGS. 6A-B, are shown in FIGS. 7A-B, and are also described below.)

Figure 3C:
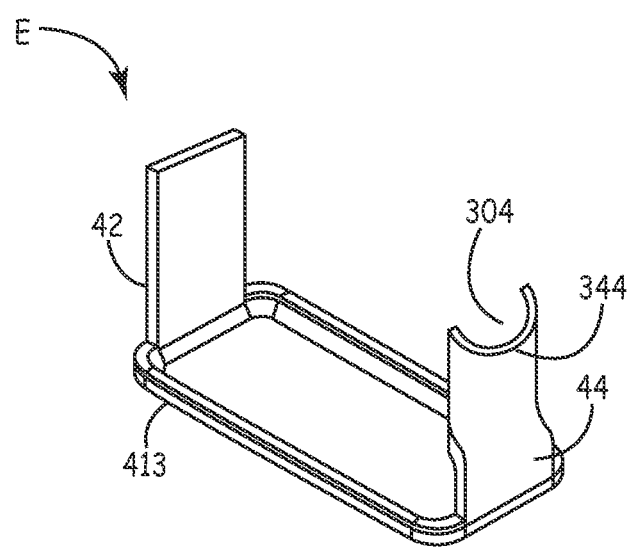
FIG. 3C is a perspective view of a conductive component, according to an alternate embodiment of the present disclosure.
Figure 4A:
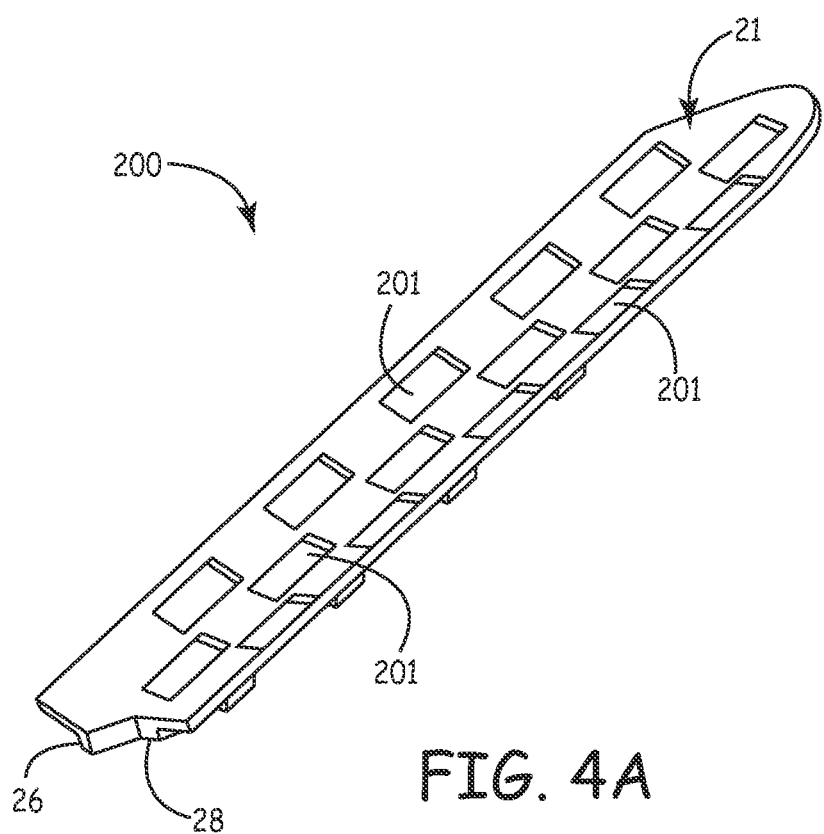
FIG. 4A is a perspective view of an insulative carrier showing a first side thereof, according to some embodiments of the present disclosure.

According to the embodiments illustrated in FIGS. 3A-B, the surface of the first side 21, against which surface 41 of electrode portion 413 is disposed, is recessed; and, with reference to FIG. 4A, it may be seen that first side 21 of carrier 200 includes a recess 201 for each electrode portion 413, for example electrodes AE1-8 and BE1-8 (FIG. 1A). It should be noted that embodiments of the present disclosure need not include recesses 201. FIGS. 3A-B further illustrate a conductor 50 coupled to tab 44 of component E by a joint 35, which may be any suitable type of joint known to those skilled in the art, for example, a weld or a crimp or a combination thereof wherein a sleeve is crimped to conductor 50 and then the crimped sleeve is welded to tab 44. Although FIGS. 3A-B show joints 35 formed on a surface of tab 44 that faces away from second side 22, some alternate embodiments include joints formed along a surface of a tab that faces toward second side 22 of carrier 200, when the tab is bent to couple the corresponding component E to carrier 200. According to one alternate embodiment of component E, tab 44 is pre-formed to accommodate crimping of conductor 50 thereto, for example as illustrated in FIG. 3C. FIG. 3C shows tab 44 including a curved portion 344 forming a groove 304, into which groove 304 conductor 50 may be inserted for crimping therein, either prior to, or following, the bending of tab 44 to couple component E to carrier 200. It should be noted that, although tab 42 is shown, in FIG. 3C, without a similar a pre-formed curve, tab 42 may also be pre-formed as tab 44.

Referring back to FIGS. 3A-B, conductor 50 is shown extending from joint 35 into a pre-formed channel 55 along second side 22 of carrier. With reference to FIG. 4B, an entirety of second side 22 of carrier 200, according to one embodiment, may be seen. FIG. 4B illustrates a plurality of pre-formed channels AG1-8 and BG1-8 (each corresponding to channel 55 illustrated in FIGS. 3A-B and 7A-B); each channel AG1-8 and BG1-8 is shown extending from a corresponding pre-formed recess 202 that accommodates a pair of tabs 42, 44. According to the illustrated embodiment, channels AG1-8 and BG1-8 direct each conductor 50 from the corresponding joint 35 (FIGS. 3A and 5) into either a first or second longitudinally extending pre-formed channel 26, 28.

Figure 4D:
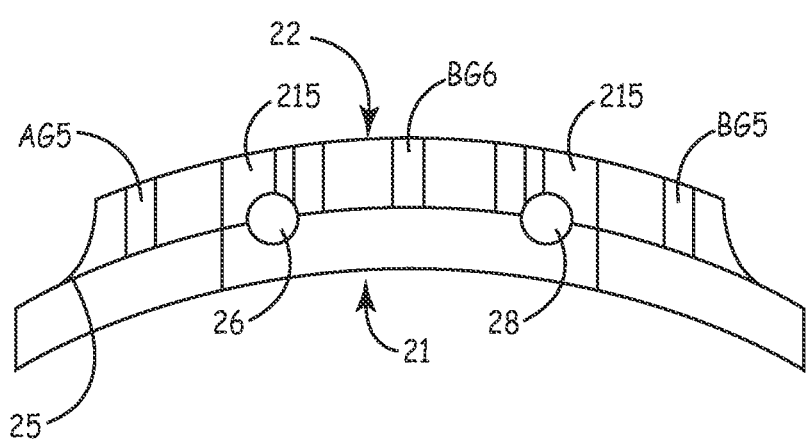
FIG. 4D is an end view of the carrier shown in FIGS. 4A-C.

FIG. 4B shows first longitudinally extending pre-formed channel 26 extending from each of channels AG1-8, and second longitudinally extending pre-formed channel 28 extending from each of channels BG1-8. FIG. 4C is an enlarged view of a portion of carrier 200 enclosed in the box shown in FIG. 4B. With reference to FIG. 4B-C, it may be seen that a series of flaps 215 extend in a zipper-like fashion over each of channels 26 and 28; conductors 50 may be pressed across flaps 215 into channels 26,28 and then held in place by flaps 215. FIG. 4D is a distal end view of carrier 200 showing flaps 215 extending over channels 26 and 28.

FIG. 4D further illustrates a panel 25, for example, formed from a polyester mesh material, extending just beneath recessed surfaces of second side 22 of carrier 200. According to some alternate embodiments, panel 25 extends just beneath an exterior surface of first side 21. According to preferred embodiments of the present disclosure, panel 25 is integrally formed with carrier 200, having a foot print similar to that of carrier 200, for example, as defined by the dashed lines in FIG. 1A, to provide some additional tear resistance to carrier 200.

Figure 5A:
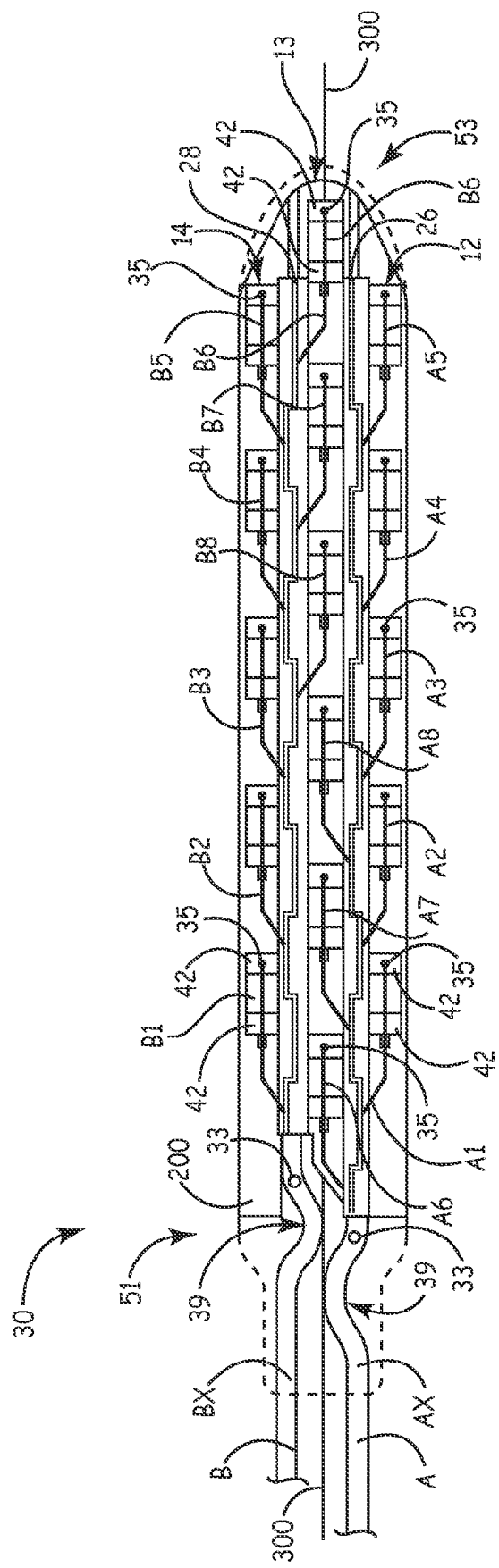
FIG. 5A is a plan view of a portion of an electrode assembly, according to some embodiments of the present disclosure.

FIG. 5A is a plan view of an electrode assembly 30, incorporating carrier 200, wherein conductors 50 (FIGS. 3A-B and 7A-B) are designated as a first plurality A1-8 and a second plurality B1-8, and dashed lines indicate a border of insulative layer 170, which has been made transparent in order to show a routing of conductors A1-8 and B1-8. FIG. 5A illustrates both of channels 26 and 28 extending approximately parallel to a longitudinal axis 300 of carrier 200, channel 26 between columns 12 and 13 to direct conductors A1-8 into tubular body A, and channel 28 between columns 13 and 14 to direct conductors B1-8 into tubular body B. According to the illustrated embodiment, each joint 35 is provided with some strain-relief against longitudinal loading by pre-formed channels AG1-8 and BG1-8 (FIG. 4B), which direct conductors A1-8 and B1-8, at an angle to longitudinal axis 300, away from respective joints 35, and into respective longitudinal channels 26, 28.

FIG. 5A further illustrates tubular bodies A and B each including a distal portion AX and BX, respectively; and, with reference to FIG. 5A in conjunction with FIG. 1A, it may be appreciated that portions AX and BX extend into proximal portion 151 of body 101 formed by insulative layer 170; layer 170 may further extend into pre-formed apertures 33 formed in sidewalls of portions AX, BX. It should be understood that portions AX and BX form extensions of the one or more longitudinal channels, or lumens, of tubular bodies A, B so that conductors A1-8 and B1-8, respectively may pass proximally therethrough from channels 26, 28. FIG. 5A further illustrates each portion AX, BX including a curved segment 39, wherein segments 39 are longitudinally offset from one another, and an apex of each segment 39 is approximately aligned with one another in close proximity to longitudinal axis 300. The illustrated u-shape of each segment 39, and the arrangement of segments 39 may facilitate compact coupling of segments 39 to carrier 200, within layer 170; however, the scope of the present disclosure is not so limited, and any suitable curved shape and arrangement can be incorporated in alternate embodiments. Curved segments 39 may provide addition strain-relief and minimize flex-fatigue for the conductors A1-8, B1-8, and may further prevent longitudinal forces from dislodging electrode assembly 30 from an implanted location. According to exemplary embodiments, tubular bodies A, B are each formed from a polyurethane material and insulative layer 170 is formed from a silicone material; because silicone and polyurethane materials may not bond to one another, the mechanical interlocking between layer 170 and tubular bodies A,B, at apertures 33 and along curve segments 39, may provide additional structural integrity to assembly 30, for these exemplary embodiments.

Figure 5B:
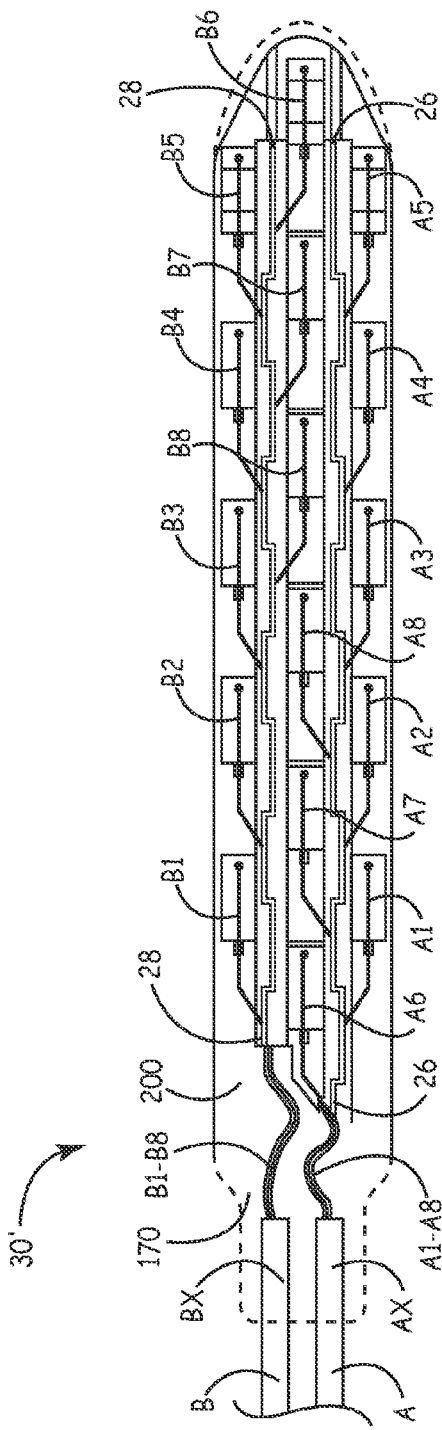
FIG. 5B is a plan view of a portion of an electrode assembly, according to some alternate embodiments of the present disclosure.
Figure 5C:
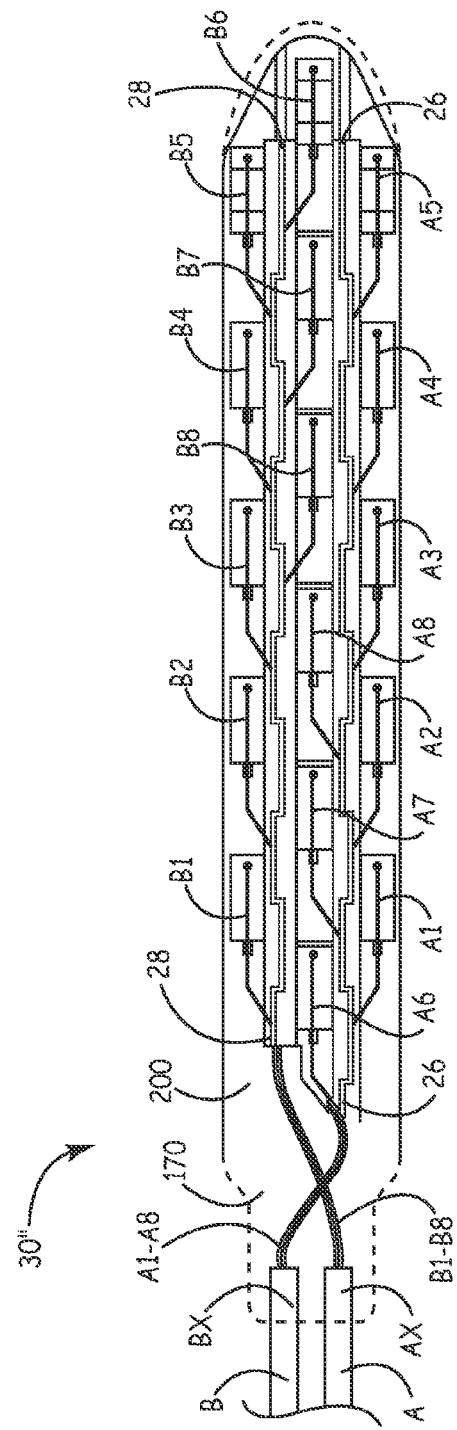
FIG. 5C is a plan view of a portion of an electrode assembly, according to yet further alternate embodiments.

FIGS. 5B-C are plan views of alternative electrode assemblies 30' and 30", respectively. FIGS. 5B-C illustrate portions AX and BX, of tubular bodies A and B, respectively, within insulative layer 170, including no curved segments, such as segments 39 illustrated in FIG. 5A. According to the embodiment of FIG. 5B, first plurality of conductors A1-8 are formed in a bend between channel 26 and portion AX, and second plurality of conductors B1-8 are likewise formed in a bend between channel 28 and portion BX. According to the embodiment of FIG. 5C, first plurality of conductors A1-8 cross over from channel 26 to enter tubular body B and second plurality of conductors B1-8 cross over from channel 28 to enter tubular body A. Conductors A1-8 and B1-8 may be held in the illustrated configurations by additional channels formed in carrier 200 or may be positioned as such prior to molding of insulative layer 170 thereover. It should be noted that embodiments of the present disclosure may further include those in which conductors A1-8, B1-8 extend in approximately straight paths from channels 26 and 28 into respective tubular bodies A, B. It should be noted that each conductor of pluralities A1-8 and B1-8 are electrically isolated from one another by an insulating jacket extending around each conductor.

Although FIGS. 5A-C illustrates a preferred embodiment wherein joints 35 are made between a distally located tab of each component E and the corresponding conductor, the scope of the present disclosure is not limited to any particular orientation of tabs 42 and 44, with respect to proximal and distal ends 51 and 53, respectively, of carrier 200; for example, some alternate embodiments include conductive components E oriented in carrier such that tabs 42, 44 are disposed on opposite sides of a longitudinal axis of the corresponding column 12, 13, 14. According to further alternate embodiments, joints 35 are made with the proximally located tabs shown in FIG. 5A; or joint 35 may be made with a centrally located tab, for example, tab 46 shown in FIG. 7B for the embodiment of component E illustrated in FIG. 6B.

FIGS. 6A-B are perspective views of conductive component E, according to additional alternate embodiments of the present disclosure; and FIGS. 7A-B are section views taken through section line D-D of FIG. 1A, according to embodiments that generally correspond to the embodiments of components E illustrated in FIGS. 6A-B, respectively. FIG. 6A illustrates component E including tabs 47 and 49 extending outward such that tabs 47, 49, when component E is coupled to carrier 200, extend along a surface of second side 22 of carrier 200, which is offset from inward facing surface 41 of electrode portion 413, for example as illustrated in FIG. 7A. According to the illustrated embodiment, tabs 47, 49 are pre-formed prior to insertion through carrier 200, however, according to an alternate embodiment, tabs 47, 49 are bent outward after insertion through carrier 200. Dashed lines in FIG. 6A illustrate yet another alternative embodiment of component E, wherein tabs 47, 49 extend both inward, toward one another, and outward. FIG. 6B, as previously described, illustrates component E including centrally located tab 46 extending from electrode portion 413; tab 46 is shown including a projection 460 which extends toward a surface of second side 22 of carrier when tab 46 is bent, as illustrated in FIG. 7B. Of course tab 46 need not include projection 460, and, according to alternate embodiments, tab 46 may be pre-formed, as shown in FIG. 7B, prior to insertion through carrier 200. Those skilled in the art will recognize that various numbers and configurations of tabs, extending from electrode portion 413 of component E, may be employed within the scope of the present disclosure.

Figure 8:
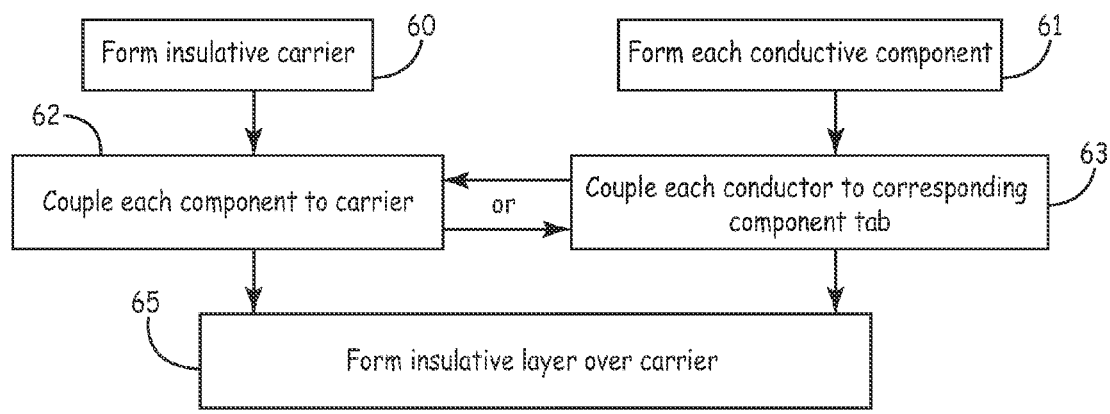
FIG. 8 is a flow chart outlining methods of the present disclosure.

FIG. 8 is a flow chart outlining alternate methods of the present disclosure for making inventive electrode assemblies. FIG. 8 outlines methods wherein forming an insulative carrier, for example carrier 200, is one initial step 60 and forming each conductive component, for example, component E, is another initial step 61. After each component and the carrier is formed, a conductor is coupled to a tab of the corresponding component, per step 63, either before or after each component is coupled to the carrier, per step 62. In a latter step 65, an insulative layer is formed over the carrier to encapsulate each component tab and conductor. According to preferred methods, the carrier is formed (step 60) via a molding process, for example, transfer or injection molding, and a polymer mesh panel, for example, panel 25 (FIG. 3D), is integrated into the carrier by inserting the panel into a mold prior to completing the molding process. A mold, which is used by some methods, includes features to form openings through the carrier and channels and recesses on first and second sides of the carrier, which openings, channels and recesses are described above in conjunction with carrier 200. According to some alternate methods, a process secondary to molding may be used to form channels and/or recesses, for example, by other types of thermal forming known to those skilled in the art, or by cutting or abrading methods, or by bonding additional layers to the molded carrier. For those embodiments of the carrier which include pre-formed openings, for example, openings 212, corresponding openings may be formed in the mesh panel prior to placing the panel in the mold, the panel openings being aligned with mold features for forming the openings of carrier, when the panel is placed.

Forming each conductive component (step 61) may be performed as described in conjunction with FIGS. 2A-B, and coupling each component to the carrier (step 62) is performed by inserting one or more tabs of the component through the carrier such that an electrode portion of the component is disposed on the first side of the carrier and the one or more tabs are disposed on the second side of the carrier to secure the component to the carrier, for example as illustrated in FIGS. 3A-B and 7A-B. The one or more tabs may be bent, after insertion through the carrier, or pre-formed in a bent configuration, prior to insertion through the carrier, such that bending the tabs after insertion through the carrier is not required to secure the component to the carrier. According to a preferred method of the present disclosure, the tabs of all of components E are bent or folded simultaneously after having been inserted through the carrier. All the tabs may be simultaneously folded by a plate that is pressed down toward the second side of the carrier while the components are supported, for example, along contact surfaces 43 of electrode portions 413.

According to some methods, after each component is coupled to the carrier (step 62), each conductor is coupled to the corresponding component tab, per step 63. According to some alternate methods, each conductor is coupled to the corresponding component tab (step 63) prior to coupling each component to the carrier (step 62). If step 62 follows step 63, a length of the conductor may be passed through the carrier ahead of the tab to couple the component to the carrier, or, the electrode portion of the component may be passed through the carrier, ahead of the tab. Although not shown in the outline of FIG. 8, each conductor may be routed in grooves on the second side of the carrier either before or after coupling each conductor to the corresponding component tab. As previously described in conjunction with FIGS. 4B-D, FIG. 5A, and method step 60, insulative carriers, according to some preferred embodiments of the present disclosure, include pre-formed channels which are suitable for routing conductors along the carrier to insulative tubular bodies and have features to hold conductors in place on the carrier while the insulative layer is formed over the carrier (step 65). Such channels may further provide some strain-relief for the coupling between each conductor and the corresponding component tab. Coupling each conductor to the corresponding component tab, per step 63, may be performed by any of the methods previously described, for example, by crimping, welding (e.g. laser or resistance), or a combination thereof, or by any other suitable method known to those skilled in the art.

Once each component and corresponding conductor, coupled thereto, are mounted or coupled to the carrier, an insulative layer may be formed, per step 65, over the side of the carrier on which the component tabs and conductors are disposed. As previously described, the insulative layer may further surround a portion of one or more elongate tubular bodies into which each conductor has been inserted, for example, portions AX, BX of tubular bodies A, B shown in FIGS. 5A-C. Each conductor may have been inserted into the corresponding tubular member at any point, before step 65, in the method outlined by FIG. 8, that is, before or after any of steps 60, 61, 62, and 63. According to some methods of the disclosure, prior to insertion of each conductor into the corresponding tubular body, each tubular body is thermal formed to include a curved segment, for example segment 39, shown in FIG. 5A, and may also be perforated to include an aperture, for example aperture 33, also shown in FIG. 5A. Forming the insulative layer (step 65) is preferably performed by an over-molding process, for example, either by injection molding or transfer molding. According to the over-molding process, the carrier on which each electrode and corresponding conductor are mounted, along with each tubular body, in which each corresponding conductors has been inserted, are placed in a mold, and an insulative material, preferably silicone rubber, is injected into the mold to cover each conductor and component tab, for example, along second side 22 of carrier 200, and to surround each tubular body, for example, as illustrated in FIGS. 1A and 5A-C.

In the foregoing detailed description, the disclosure has been described with reference to specific embodiments. However, it may be appreciated that various modifications and changes can be made without departing from the scope of the disclosure as set forth in the appended claims.

The invention claimed is:

1. An implantable medical system, comprising:
    a stimulation device; and
    an electrical paddle lead that comprises:
        an insulative carrier including a first side and a second side opposite the first side;
        a plurality of conductive components, each of the conductive components including at least one tab and an electrode portion having an inward facing surface and an outward facing contact surface, the electrode portion of each conductive component being disposed on the first side of the carrier, each tab of each conductive component extending away from the corresponding electrode portion through the carrier and bending to extend along the second side of the carrier to secure the conductive component to the carrier, the electrode portions arranged in at least one column, the carrier extending beneath at least a portion of the electrode portion of each conductive component;
        at least one elongate insulative tubular body having an end with a plurality of contacts that are electrically connected to the stimulation device;
        a plurality of conductors extending within the at least one elongate insulative tubular body, each of the plurality of conductors being electrically coupled to a corresponding one of the plurality of contacts and to a corresponding one of the conductive components, the conductive components being powered by the plurality of contacts being electrically connected to the stimulation device; and
        an insulative layer molded over the tabs and the second side of the carrier to form a first side of a paddle-shaped body of the implantable medical electrical paddle lead.

2. The medical system of claim 1, wherein the at least one elongate insulative tubular body comprises a pair of elongate insulative tubular bodies each having a respective one of the at least one connector.

3. The medical system of claim 1, wherein each outward facing contact surface of the plurality of conductive components is on a second side of the paddle-shaped body opposite the first side of the paddle-shaped body.

4. The medical system of claim 1, wherein the at least one tab of each conductive component comprises a pair of tabs.

5. The medical system of claim 1, wherein the at least one column comprises a plurality of longitudinally extending columns of the electrode portions.

6. The medical system of claim 1, wherein the paddle lead has a shape and a profile suitable for epidural implantation to provide spinal cord stimulation.

7. The medical system of claim 1, wherein each of the conductors includes an insulating jacket extending over the conductor.

8. The medical system of claim 1, wherein the carrier comprises a polymer mesh.

9. The medical system of claim 1, wherein the insulative layer is bonded to the second side of the carrier.

10. The medical system of claim 1, wherein the carrier has pre-formed openings sized to accommodate the tabs which extend there through.

11. The medical system of claim 1, wherein the insulative layer surrounds a portion of the at least one elongate tubular body.

12. The medical system of claim 1, wherein the insulative layer is coupled to each of the at least one tab of each of the conductive components.

13. The medical system of claim 1, wherein each of the conductors is in the form of a coil or a cable.

14. The medical system of claim 1, wherein each of the conductors is in electrical contact with a respective one of the at least one tab of the plurality of conductive components.

15. The medical system of claim 1, wherein:
    the at least one column comprises a first longitudinally extending column, a second longitudinally extending column, and a third longitudinally extending column, the third column being disposed between the first and second columns; and
    the plurality of conductive components is divided into a first set of components, a second set of components, and a third set of components, each electrode portion of the first set of components being arranged in the first column, each electrode portion of the second set of components being arranged in the second column, and each electrode portion of the third set of components being arranged in the third column.

16. A method of constructing an implantable medical lead, comprising:
    providing an insulative carrier including a first side and a second side opposite the first side;
    providing a plurality of conductive components, each of the conductive components including at least one tab and an electrode portion having an inward facing surface and an outward facing contact surface;
    coupling the plurality of conductive components to the insulative carrier with the electrode portion of each conductive component being disposed on the first side of the carrier, each tab of each conductive component extending away from the corresponding electrode portion through the carrier and bending to extend along the second side of the carrier to secure the conductive component to the carrier, the electrode portions arranged in at least one column, the carrier extending beneath at least a portion of the electrode portion of each conductive component;
    providing at least one elongate insulative tubular body having an end with a plurality of contacts that are configured to be electrically connected to a stimulation device;
    providing a plurality of conductors extending within the at least one elongate insulative tubular body;
    electrically coupling each of the plurality of conductors to a corresponding one of the plurality of contacts and to a corresponding one of the conductive components; and
    molding an insulative layer over the tabs and the second side of the carrier to form a first side of a paddle-shaped body of the implantable medical electrical paddle lead.

* * * * *